United States Patent [19]
Rasmussen et al.

[11] Patent Number: 5,415,627
[45] Date of Patent: May 16, 1995

[54] SYSTEM FOR DELIVERING A TACKY WOUND DRESSING

[75] Inventors: Mark J. Rasmussen, Forney; Tod H. Schultz, Arlington; Michael B. Killeen, Jr., Coppell, all of Tex.

[73] Assignee: Wilshire Technologies, Inc., Dallas, Tex.

[21] Appl. No.: 173,758

[22] Filed: Dec. 23, 1993

[51] Int. Cl.⁶ .......................................... A61F 15/00
[52] U.S. Cl. ........................... 602/57; 602/42; 602/56; 206/441
[58] Field of Search ............... 602/41, 42, 52, 56, 602/57, 58; 206/440, 441

[56] References Cited

U.S. PATENT DOCUMENTS

| | | | |
|---|---|---|---|
| 2,924,331 | 2/1960 | Hoey | 206/441 |
| 2,969,057 | 1/1961 | Simmons | 128/2 |
| 3,349,765 | 10/1967 | Blanford | 128/132 |
| 3,425,412 | 2/1969 | Pope | 128/156 |
| 4,324,237 | 4/1982 | Buttaravoli | 128/214 |
| 4,485,809 | 12/1984 | Dellas | 128/156 |
| 4,570,627 | 2/1986 | MacConkey et al. | 128/132 |
| 4,646,731 | 3/1987 | Brower | 128/156 |
| 4,650,705 | 3/1987 | Ghodsian | 428/40 |
| 4,744,355 | 5/1988 | Faasse, Jr. | 128/156 |
| 4,747,401 | 5/1988 | Potter et al. | 128/156 |
| 4,753,232 | 6/1988 | Ward | 602/57 |
| 4,807,613 | 2/1989 | Koehnke et al. | 128/155 |
| 4,837,062 | 6/1989 | Dunshee et al. | 428/41 |
| 4,884,563 | 12/1989 | Sessions | 602/57 |
| 4,909,244 | 3/1990 | Quarfoot et al. | 602/56 |
| 4,915,102 | 4/1990 | Kwiatek et al. | 128/156 |
| 4,917,112 | 4/1990 | Kalt | 128/156 |
| 4,926,850 | 5/1990 | Lott et al. | 128/155 |
| 5,012,801 | 5/1991 | Feret | 128/155 |
| 5,018,515 | 5/1991 | Gilman | 128/155 |
| 5,035,687 | 7/1991 | Sandbank | 604/180 |
| 5,042,466 | 8/1991 | McKnight | 128/155 |
| 5,074,293 | 12/1991 | Lott et al. | 128/155 |
| 5,088,483 | 2/1992 | Heinecke | 602/46 |
| 5,092,323 | 3/1992 | Riedel et al. | 602/54 |
| 5,106,629 | 4/1992 | Cartmell et al. | 424/445 |
| 5,158,555 | 10/1992 | Porzilli et al. | 604/307 |
| 5,160,328 | 11/1992 | Cartmell et al. | 604/307 |
| 5,204,110 | 4/1993 | Cartmell et al. | 424/443 |
| 5,225,199 | 7/1993 | Hidaka et al. | 424/443 |

FOREIGN PATENT DOCUMENTS

| | | | |
|---|---|---|---|
| 3809539A1 | 5/1989 | Germany | A61F 13/02 |
| 2192792 | 1/1988 | United Kingdom | A61F 13/02 |

OTHER PUBLICATIONS

I. Kelman Cohen, et al., Wound Healing, Biochemical & Clinical Aspects, W. B. Saunders Company, Harcourt Brace Jovanovich, Inc., *Library of Congress Cataloging-in-Publication Data*, 1992, pp. 562–580.

*Bertek Integrated Pouch/Patch Delivery Systems*, 1990, Bertek, Inc. (6 pages).

*Primary Examiner*—Randall L. Green
*Assistant Examiner*—Paul Prebilic
*Attorney, Agent, or Firm*—Vinson & Elkins

[57] ABSTRACT

A tacky wound dressing delivery system is disclosed that includes a film and wound dressing material which is to be applied to a patient's wound, a protective cover, which is adjacent to the film, an adhesive layer on one surface of the film, a tab located to one end of the adhesive layer, a release liner covering the adhesive layer and tacky material and tab, and a tape which is used to connect the release liner with the protective cover. The edges of the tacky wound dressing material are displaced from the edges of the system so that the tacky wound dressing material does not adhere to packing nor to any astray particles of the tacky material.

22 Claims, 3 Drawing Sheets

SYSTEM FOR DELIVERING A TACKY WOUND DRESSING

BACKGROUND OF THE INVENTION

A wound dressing is a material applied to a wound or a diseased part of the body, with or without medication, to protect and assist healing. The treatment and the healing of wounds is an art old as humanity. There are, for example, accounts of Egyptians using honey as a dressing for use in wound care management dating back to 3,000 to 2,500 B.C. The techniques and understanding of wound treatment have continued to develop since that time, and in the last decade, the understanding and treatment of wounds has significantly improved due to studies at the molecular level and due to newly developed wound care products. See generally, I. Kelman Cohen, Robert F. Diegelmann, and William J. Lindblad, *Wound Healing: Biochemical and Clinical Aspects* (1992).

A simplified model of wound healing may involve three basic stages. First, acute inflammatory events occur which limit damage and clear the stage for subsequent repair to take place. Second, formation of fibrovascular granulation tissue and the epithelialization occur. Third, remodeling and maturization of scar tissue occurs. In this process, wound dressings may be an important part of the wound treatment in helping to isolate the wound from the harmful external environment as desired, in performing a hemostasis function, and in helping to prevent wound infection. While a dressing cannot sterilize a wound, it may create a condition for reducing the pathogenic load by preventing overgrowth and colonization or by delivering antimicrobial agents to the wound (See the above-referenced article, *Wound Healing: Biochemical and Clinical Aspects*).

For certain types of wounds, it is desirable to apply a hydrocolloid, hydrogel, or other tacky wound dressing. The stickiness or tackiness of these types of wound dressings have, however, created problems in packaging the wound dressings. A problem may occur because the tacky or sticky dressing adheres to the packaging and may make removal of the package difficult, and on some occasions, could damage the wound dressing. In addition to being sticky and tacky in and of itself, the process of cutting the sticky material from which the tacky wound dressing is formed may create small sticky particles, which some people in the wound dressing industry refer to as "boogers." One conventional approach to solving the problem of packaging the tacky wound dressing has been to provide a separate tray for holding the wound dressing and then applying the external packaging material around the tray. In packaging some tacky wound dressings, a tray with a lid has been used with the tacky wound dressing sandwiched between the tray and the lid before being packaged.

In using wound dressings as a part of a wound care treatment strategy, it may be desirable in some situations to frequently change the wound dressing. Because of frequent changes of the dressings, it may be desirable to have wound dressings that are both easily administered and inexpensive. In this regard, a number of devices have appeared in the wound dressing art.

Wound dressings known in the art have not, however, provided a wound dressing or dressing delivery system that is sufficiently easy to manufacture so as to provide a relatively inexpensive dressing or delivery system. Furthermore, the wound dressings known in the art have generally been difficult to administer—at least as to wound dressings having a dressing or delivery system involving thin films. While some improvement has been made in the delivery systems for such dressings, there have been shortcomings in the designs. Prior art designs have generally called for complicated manufacturing techniques, or design features that require complicated manufacturing techniques to produce, and have frequently required the use of additional adhesive layers. This latter shortcoming, increases the chance that the health care provider will inadvertently make contact with the additional adhesive layers. Additionally, some research has suggested the importance of oxygen in wound healing, and an additional adhesive layer may adversely affect the oxygen permeability as well as the moisture vapor transmission rate (MVTR) of the film.

Thus, a need has arisen for a wound dressing delivery system that allows easy packaging and that is easily administered to a patient's wound while requiring a minimal number of adhesive layers and being relatively easy and inexpensive to manufacture.

SUMMARY OF THE INVENTION

In accordance with the present invention, a wound dressing delivery system and a method of manufacturing a wound dressing delivery system are provided that substantially eliminate or reduce the disadvantages and shortcomings associated with the prior wound dressing delivery systems and methods.

According to one aspect of the present invention, a wound dressing delivery system is provided including a film, a protective cover, which is temporarily attached to the film without requiring an adhesive therebetween, an adhesive layer attached to the film, a tab on one end of the adhesive layer, a release liner covering the adhesive layer, tape overlying and connecting a portion of the release liner and protective cover and a tacky wound dressing disposed on the film.

A technical advantage of the present invention is that it allows for convenient and easy packaging of a tacky wound dressing without requiring additional packaging trays or holders and allow for easy application of the dressing to a patient.

Another technical advantage of the present invention is that it provides a delivery system that is relatively easy to manufacture, and thus having a reduced expense associated with its manufacture. Yet another technical advantage of the present invention is that only one adhesive layer is required for the dressing delivery system, which may decrease the likelihood of inadvertent contact with an adhesive and may allow for greater oxygen permeability and a higher moisture vapor transmission rate.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

The preferred embodiment of the present invention and its advantages are best understood by referring to FIGS. 2–13 of the drawings, like numerals being used for like and corresponding parts of the various drawings.

Figure 1:
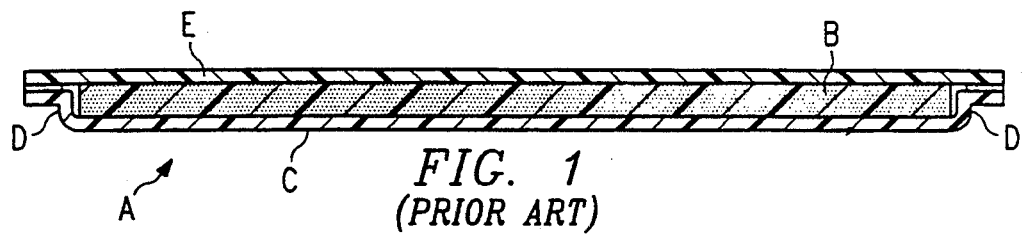
FIG. 1 is prior art tacky wound dressing packaging system in cross section.

Referring to FIG. 1, the inner portion of a packaging system A is shown. The tacky wound dressing material B is shown resting on tray C, which has side portions D. A tray lid E rests on top of the tray sides D. With this prior art system, to package the tacky wound dressing material B, the manufacturer places the material B into tray C and then covers the tray with lid E. The tray C and lid E may then be covered by a paper or plastic packaging without fear of the tacky wound dressing B adhering to the packaging or having any of the small tacky particles that are created when dressing B is cut from interfering with the external packaging. To use the dressing B of FIG. 1, the health care provider rips open the external packaging, removes lid E and then physically grabs the dressing B and applies it to the patient's wound. This system A requires numerous additional parts which may increase the expense of manufacture and is not convenient to apply the dressing B to the patient.

Figure 2:
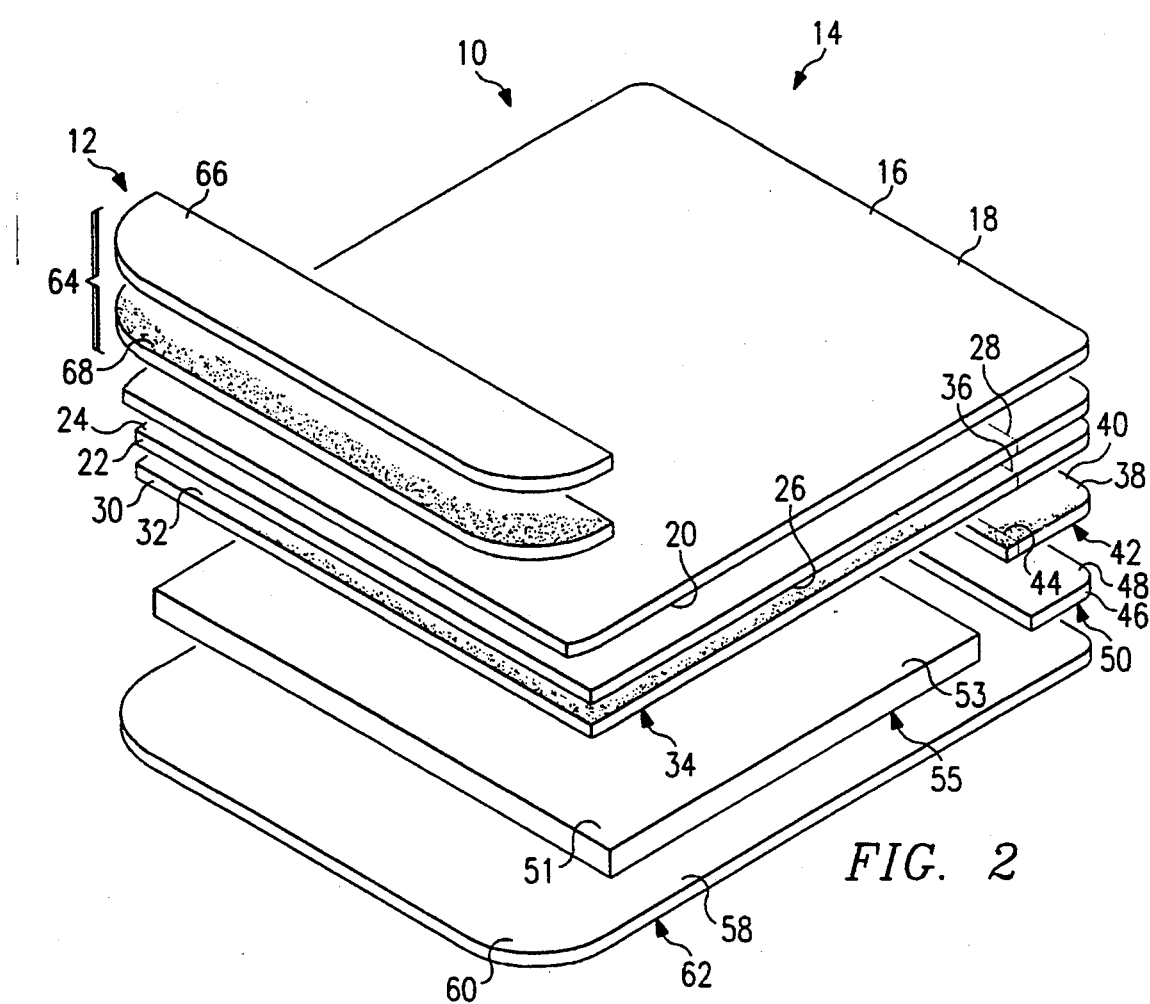
FIG. 2 is a schematic isometric exploded view of a tacky wound dressing delivery system according to one aspect of the present invention.

Referring to FIG. 2, wound dressing delivery system 10 of the present invention is shown with the components, which will be described below, shown with exaggerated thicknesses and not to scale. Wound dressing delivery system 10 has a pivot end 12 and an opening end 14. Wound dressing delivery system 10 is shown with a protective cover 16 having a first side 18 and a second side 20. A film 22 is adjacent protective cover 16. Film 22 has a first side 24 and a second side 26. A kisscut 28 is formed through a portion of film 22 proximate opening end 14. An adhesive layer 30 having a first side 32 and a second side 34 may be adjacent film 22. A kisscut 36 is made through adhesive layer 30 proximate opening end 14. A first adhesive strip 38 is shown adjacent adhesive layer 30 and proximate opening end 14. Adhesive strip 38 has a first side 40 and a second side 42. A kisscut 44 is formed through one end of adhesive strip 38. Adjacent to adhesive strip 38 is tab 46. Tab 46 has a first side 48 and a second side 50. Tacky wound dressing material 51 has first side 53 and second side 55. Adjacent to tab 46 and tacky material 51 and adhesive layer 30 is release liner 58. Release liner 58 has a first side 60 and a second side 62. Tape 64 is located on pivot end 12 and has a backing material 66 and a tape adhesive 68.

Figure 3:
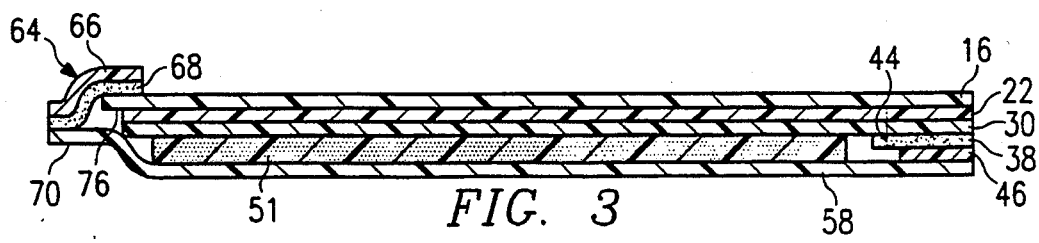
FIG. 3 is a schematic view in cross section of the wound dressing delivery system of FIG. 2.
Figure 4:
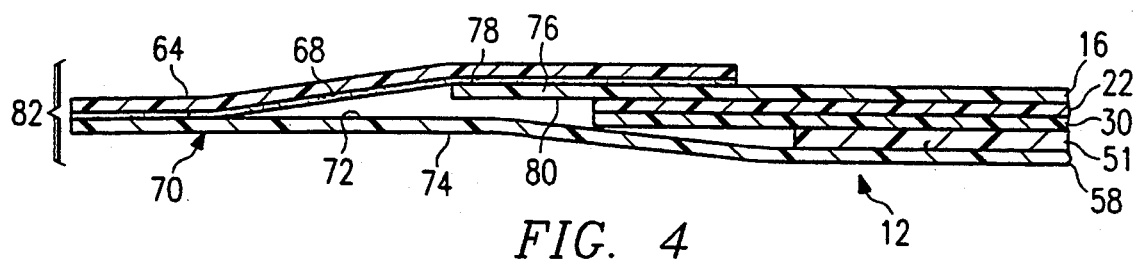
FIG. 4 is a schematic view in cross section of the pivot end 12 of the system 10 of FIG. 3.
Figure 5:
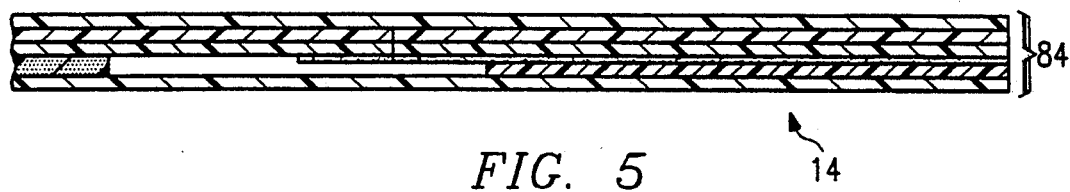
FIG. 5 is a schematic view in cross section of the opening end 14 of the system 10 of FIG. 3.

FIG. 3 shows a cross section of the components comprising one embodiment of the tacky wound dressing delivery system 10, and FIGS. 4 and 5 show pivot end 12 and opening end 14 respectively in cross section. Release liner 58 extends past the pivot end or termination edge of adhesive layer 30, film 22, material 51 and protective cover 16 to form a release liner extension 70 having a first side 72 and a second side 74. A portion of protective cover 16 extends past the pivot end or termination edge of film 22, adhesive layer 30, and material 51 to form a protective cover overhang 76, which has a first side 78 and a second side 80. Protective cover overhang 76 may prevent migration of adhesive 68 of tape 64 into contact with adhesive layer 30 near pivot end 12, which might interfere with the proper application of a wound dressing system 10.

A pivot assembly 82 (FIG. 4) is formed by tape 64, release liner overhang 70, a portion of protective cover 16 proximate pivot end 12, a portion of film 22 proximate pivot end 12, a portion of adhesive layer 30 proximate pivot end 12, and in some embodiments, could include a portion of tacky wound dressing material 51. Pivot assembly 82 connects protective cover 16 and release liner 58 in a manner that greatly simplifies the manufacturing process of system 10 while allowing simplified application of a wound dressing to a patient.

In a preferred embodiment, protective cover 16 may be a polyester material with a silicone coating on second side 20. The silicone coating which is applied to second side 20 of protective cover 16 allows film 22 to be solvent casted onto side 20 of protective cover 16. In a solvent casting sheet or protective cover 16 and heated in an oven and then the solvent is driven off; the remaining materials or solids solidify to form the appropriate substrate. The casting of film 22 onto second side 20 of protective cover 16 creates a temporary and releasable bond that provides a means for temporarily attaching second side 20 to first side 24 of film 22.

The temporary attachment is by the cohesive interaction of film 22 and protective cover 16. The ability to releasably and temporarily attach film 22 onto protective cover 16 without requiring adhesives is an important aspect of the present invention. While the preferred embodiment creates the temporary attachment of film 22 and protective cover 16 by solvent casting film 22 onto cover 16, it is to be understood that the temporary attachment may be achieved by other techniques such as extruding film 22 onto cover 16.

Protective cover 16 may be formed of any material which is suitable for use with the technique used to create the temporary and releasable bond to be produced between protective cover 16 and film 22, e.g., protective cover suitable for use with solvent casting for the preferred embodiment. A polyester material is used in the preferred embodiment for cover 16. Other suitable materials for protective cover 16 include polypropylene with a silicone coated release material or any substrate that is coated or provided to allow the temporary and releasable bond to be created and that improves the release of the material from that substrate. Another example of a suitable material for cover 16 is kraft paper with or without a silicone coating.

Adhesive layer 30 is preferably a modified acrylic adhesive that is pressure sensitive. There are, however, a plethora of adhesives that may be used as part of the present invention. Other adhesives that may be appropriate include water activated adhesives (hydroactive), hydrophobic adhesives, hydrophilic adhesives, pressure sensitive adhesives or non-pressure sensitive adhesives. Acrylic- or silicone-based, or rubber-based adhesives or modified-acrylic-based adhesives may be used. Additionally, active adhesives may be used, which include various drug or chemical components mixed with the adhesive; for example, growth factors may be included in the adhesive such as epidermal growth factor (E.G.F.), fibroblast growth factor (F.G.F.), platelet-derived growth factor (P.D.G.F.) and transforming growth factor—$\beta$ (T.G.F.—$\beta$). Adhesive layer 30 may also include a medicated ingredient such as an antimicrobial. Adhesive layer 30 may be continuous or discontinuous. The latter coverage is utilized in the preferred embodiment for adhesive layer 30. Forming adhesive layer 30 as a discontinuous layer may increase oxygen permeability and moisture vapor transmission rate of the dressing.

Tape or splice tape 64 is preferably a silicone tape. Different tapes may, however, be used. An alternative tape may be desirable for different release liners 58. As will be described more fully below, tape 64 is placed over release liner overhang 70 and protective cover overhang 76 to connect overhangs 70 and 76 in a manner that may be easily executed during the manufacturing process. As shown in FIG. 3, release liner overhang 70 may extend beyond protective cover overhang 76 with tape 64 connecting overhangs 70 and 76 from the top for the orientation shown in FIG. 3. An alternative embodiment of this aspect of pivot assembly 82 is utilized in the embodiment shown in FIG. 8.

Tacky wound dressing material 51 may be a hydrogel, hydrocolloid or other sticky or tacky material. Material 51 may include active ingredients such as growth factors or components such as calcium, sodium, chitin, zinc, or derivatives thereof, and/or various alginates, whether natural or synthetic. Additional, if a hydrogel is used for material 51, it may be hydrated or dehydrated and may be with growth factors or the other components mentioned above.

Figure 6:
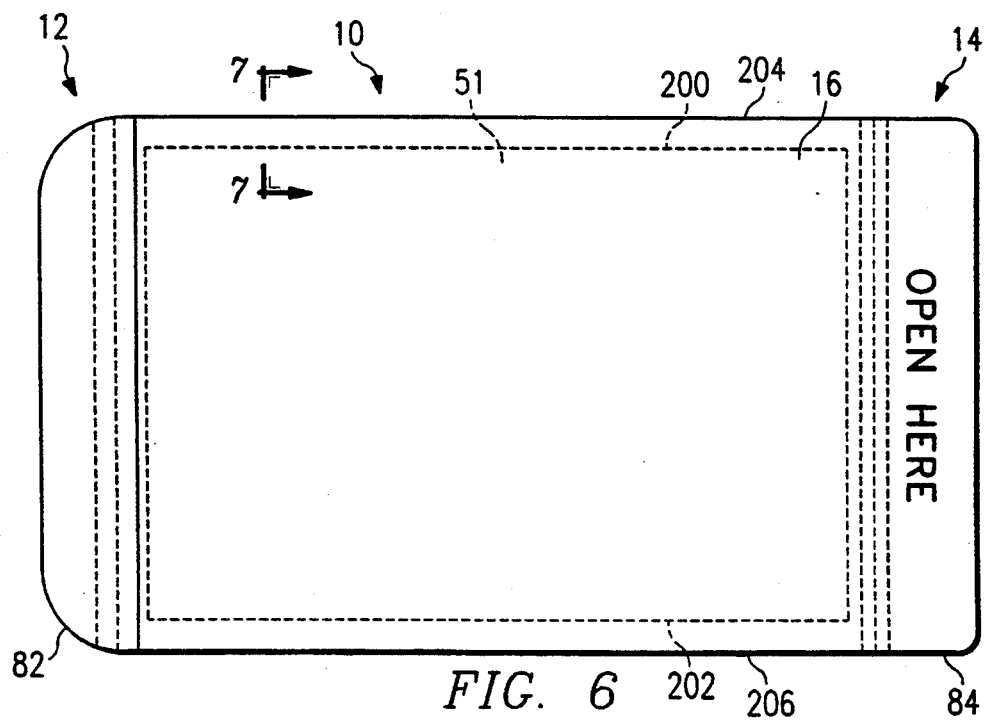
FIG. 6 is a plan view of the tacky wound dressing system of FIGS. 2 through 5.

The relative strengths of the cohesive forces involved in system 10 are an important aspect of the present invention. In applying wound dressing delivery system 10, it is necessary that the cohesive interaction between protective cover 16 and film 22 resulting from the temporary and releasable bond have a smaller cohesive force than is developed between adhesive layer 30 and a patient's wound or flesh and between material 51 and the patient's wound or flesh. Because the cohesive force between adhesive layer 30/material 51 and the patient is greater than the cohesive force developed by film 22 and protective cover 16, as protective cover 16 is pulled away from the patient, protective cover 16 will release or separate from film 22 before adhesive layer 30 and material 51 release from the patient's wound or skin. Additionally, the cohesive force developed between adhesive layer 30 and second side 26 of film 22 must likewise be greater than the cohesive force developed between film 22 and protective cover 16. The adhesive layer 30, which extends beyond material 51 as shown in FIG. 6, adheres to the patient while protective cover 16 is removed from film 22. The cohesive forces developed between the material 51 and the patient's wound, and between the material 51 and the adhesive layer 30 may also be greater than the cohesive force developed between film 22 and protective cover 16.

One means of assuring that the cohesive force between adhesive layer 30 and the patient's wound or skin is greater than the other mentioned cohesive forces, is to provide additional adhesive strips such as adhesive strip 38 onto adhesive layer 30; strip 38 will increase the cohesive force between adhesive layer 30 and the skin or wound. Adhesive strip 38 may be formed of the same adhesive material from which adhesive layer 30 is formed. Similarly, an additional adhesive strip could be applied on the second side 34 of adhesive layer 30 proximate pivot end 12.

In an alternative embodiment, adhesive strip 38 is not required, but an adhesive, which forms adhesive layer 30, is used that readily develops a cohesive force that is greater than the cohesion force of the releasable bond between protective cover 16 and film 22.

Figure 8:
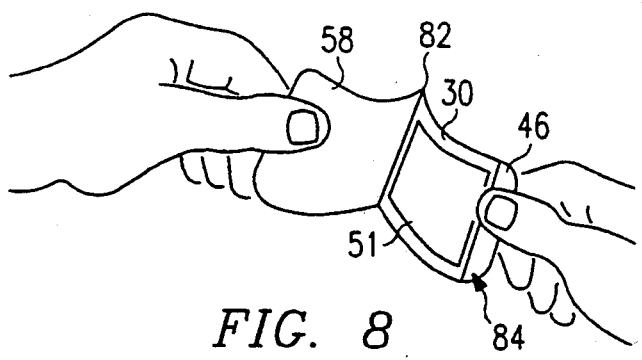
FIG. 8 is a schematic of the tacky wound dressing delivery system of FIGS. 2–6 showing the removal of the release liner from the adhesive layer.
Figure 9:
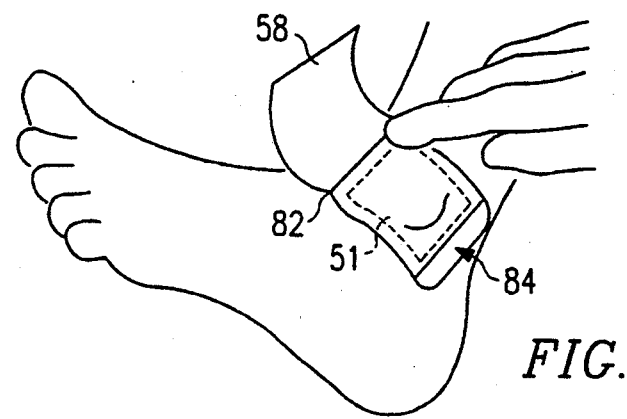
FIG. 9 is a schematic view of the tacky wound dressing delivery system of FIGS. 2–6 showing the application of the tacky dressing material and the adhesive layer and the film surrounding the tacky material to the wound of a patient.

Tab 46 facilitates application of system 10 to a patient and provides a barrier to prevent the physician or medical care provider's hand from coming into contact with the adhesive of adhesive layer 30. When tab 46 is pulled away from a portion of release liner 58 proximate opening end 14, a force may be developed that pulls release liner 58 away from adhesive layer 30 to allow adhesive layer 30 to be exposed for application to the patient. See FIG. 8. As shown clearly in FIGS. 3 and 5, tab 46 may be placed over first adhesive strip 38. Tab 46 may be any non-releasable or release-resistant material, but is preferably a paper strip. As shown in FIGS. 2 and 5, tab 46 is sized and placed so that an edge of tab 46, which is closest to pivot end 12, is spaced from kisscut 44. The arrangement of tab 46 relative to adhesive strip 38 and adhesive layer 30 allows a portion of adhesive strip 38, which is to the left of kisscut 44 for the orientation shown in FIG. 3, to contact the patient when applied as shown in FIG. 9; the portion of adhesive strip 38 in contact with the patient assures that the cohesive force there will be stronger than the cohesive force between protective cover 16 and film 22. As previously noted, if the cohesive force of adhesive layer 30, or adhesive layer 30 in combination with tacky wound dressing material 51, creates a sufficiently strong cohesive force, configuring the system 10 to allow portion of adhesive strip 38 to come into contact with the patient may be unnecessary.

Referring to FIG. 5, a handle assembly 84 is formed by tab 46, a portion of first adhesive strip 38, a portion of adhesive layer 30 proximate opening end 14, and a portion of film 22 proximate opening end 14. Handle assembly 84, in conjunction with pivot assembly 82, greatly facilitates the application of film 22 to a wound or the skin of a patient. Handle assembly 84 may be gripped or held by one hand of the physician or health care provider while the other hand is used to pull and hold release liner 58 to facilitate applying adhesive layer 30 and material 51 to the patient's wound or skin as shown in FIGS. 8–11. Handle assembly 84 may be removed from system 10 after application of film 22 to the patient as shown in FIG. 11.

For the purpose of removing handle assembly 84, kisscuts 28, 36, 44 may be placed through portions of handle assembly 84. Film 22 has kisscut 28. Adhesive layer 30 has kisscut 36. First adhesive strip 38 has kisscut 44. Kisscuts 28, 36, and 44 allow handle assembly 82 to be removed from other portions of system 10 after protective cover 16 is removed as shown in FIG. 11.

Yet another important aspect of system 10 is kisscut 44 through first adhesive strip 38. The portions of adhesive strip 38 adjacent to and along each side of kisscut 44 migrate on to each other and provide an adhesive force between adhesive layer 30 and tab 46. When the health care provider is preparing system 10 for application, the health care provider pulls release liner 58 away from handle assembly 84 as shown in FIG. 8, and this causes the cohesive force developed in first adhesive strip 38 adjacent kisscut 44 to allow a force to be developed on side 26 of film 22 which facilitates removal of layer 30 from release liner 58 without causing or tending to cause film 16 to separate from film 22.

Release liner 58 may be any suitable release means for covering adhesive layer 30 and material 51 and protecting adhesive layer 30 and material 51 from contaminates and allowing development of a cohesive force between adhesive layer 30 and liner 58 that is smaller than the cohesive force between adhesive layer 30 and film 22 and between film 22 and protective cover 16. Release liner 58 also develops a cohesive force between material 51 and release liner 58 that is smaller than the cohesive force between material 51 and adhesive layer 30. The cohesive forces between adhesive layer 30/material 51 and release liner 58 may be the smallest of the cohesive forces in system 10. If an active ingredient is included with adhesive layer 30 and/or material 51, release liner 58 should be appropriately selected to act as a barrier to the active ingredient. In the preferred embodiment, a paper with a silicone coating on first side 60 is utilized for release liner 58.

Film 22 (and possibly additional substances as discussed below) with adhesive layer 30 on second side 26 of film 22 and wound dressing material 51 from the wound dressing that remains on the patient as a final result of using wound dressing delivery system 10. In the preferred embodiment, film 22 is a polyurethane film, but numerous films may be used for film 22 according to the desired treatment of the patient's wound. For example, polypropylene may also be used for film 22. Film 22 may have different characteristics according to its intended use; for example, film 22 may be permeable, impermeable, semi-impermeable, or occlusive, non-occlusive, or semi-occlusive. The material of film 22 may be a woven, non-woven, or knitted material. Film 22 may be any thin suitable material such as polyurethane, polypropylene, hydrocolloids with or without active ingredients such as growth factors or components such as calcium, sodium, chitin, zinc, or derivatives thereof, and/or various alginates, whether natural or synthetic. Additionally, film 22 may include or be formed as hydrated or dehydrated hydrogels which may include the active ingredients and components described above for the hydrocolloids. Film 22 may be transparent to allow for viewing of the patient's wound during the application of the dressing to the wound, or to view the wound after the dressing has been applied to the extent possible through material 51.

Figure 7:
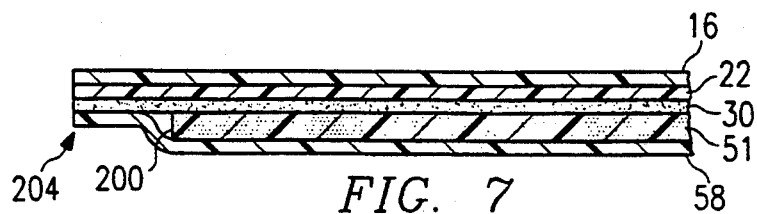
FIG. 7 is a schematic cross sectional view in proportion of the longitudinal edge of the tacky wound dressing delivery system of FIG. 6.

Referring now to FIG. 6, a schematic plan view of system 10 is shown. Tacky wound dressing material 51 is shown in hidden lines, and it can be seen that in the preferred embodiment, the longitudinal edges 200 and 202 are displaced from the longitudinal edges 204 and 206 of system 10. A portion of the longitudinal edges 200 and 204 are shown in FIG. 7 in cross section. The displacement of longitudinal edges 200 and 202 from longitudinal edges 204 and 206 of system 10 helps to assure that the tacky material 51 or any stray portions of the material 51 developed during the cutting process ("boogers") will not extend beyond the protective cover 16 or release liner 58. This latter feature allows system 10 to be packaged directly without concerns of the system, particularly substance 51 or any boogers from adhering to the external packaging. Thus, a packaging tray, such as tray C of FIG. 1, is not necessary with system 10.

Referring to FIGS. 8 through 11, the application of the first embodiment (FIGS. 2-7) of the wound dressing delivery system 10 of the present invention is shown being applied to a patient. Referring to FIG. 8, the health care provider holds a portion of release liner 58 that overhangs or is adjacent to tab 46 on opening end 14, and grabs tab 46 of handle assembly 84 and pulls the two apart. This pulling action causes release liner 58 to be removed from adhesive layer 30 and material 51, while maintaining the other layers 30, 22, 51 and 16 as they were because of the relative strength of the cohesive forces previously discussed. Release liner 58 is pulled until it reaches pivot assembly 82 so that adhesive layer 30 and tacky wound dressing material 51 is exposed.

Referring to FIG. 9, the now exposed adhesive layer 30 and material 51 are placed over the portion of the patient's body to be covered by the dressing (film 22, material 51 and adhesive layer 30. Pressure may then be applied by the health care provider to first surface 18 of protective cover 16 along the edges thereof to allow adhesive layer 30 and material 51 to make good contact with the patient.

Figure 10:
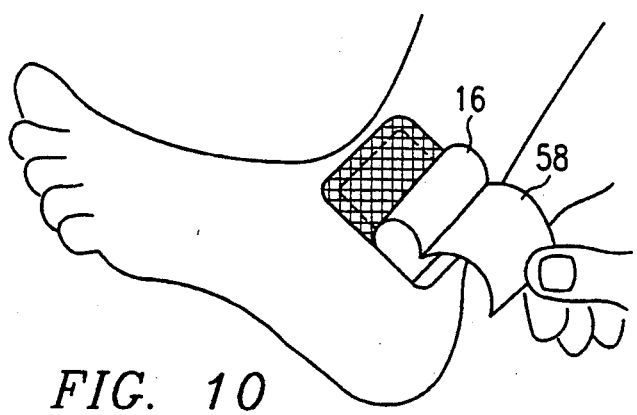
FIG. 10 is a schematic view of the tacky dressing delivery system of FIGS. 2–6 showing the removal of the protective cover from the film of the delivery system.
Figure 11:
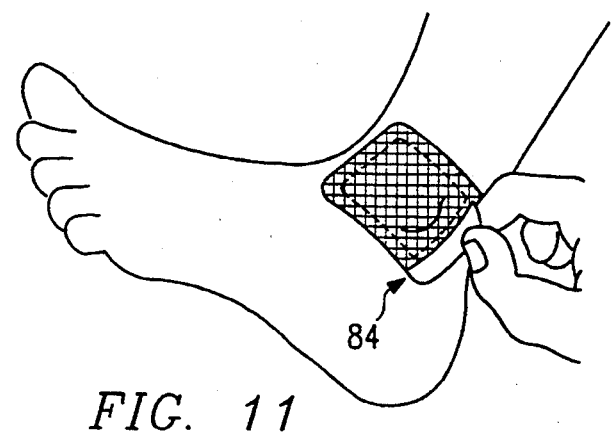
FIG. 11 is a schematic view of the wound dressing delivery system of FIGS. 2–6 showing removal of the tab from the film.

Referring to FIG. 10, the health care provider may then pull release liner 58 away from the patient as shown which causes the releasable bond between film 22 and protective cover 16 to be severed or released because of the relative strength of the cohesive forces as previously described. The health care provider continues to pull liner 58 until release liner 58 and protective cover 16 are completely removed from film 22.

Then, as shown in FIG. 11, handle assembly 84 may be easily removed from the remaining portion of film 22, material 51, and adhesive layer 30 because of kisscuts 28, 36, and 44 through the portions of handle assembly 84. The health care provider removes handle 84 by pulling on handle 84 away from film 22; this pulling by the health care provider creates a force on handle 84 away from film 22 which separates handle 84 from film 22, adhesive layer 30, and first adhesive strip 38 along kisscuts 28, 36 and 44. Thus, the dressing is easily administered to the patient by wound dressing delivery system 10, which is easily manufactured.

The ease with which the present system may be manufactured compared to systems previously known is one of the major advantages of the wound dressing delivery system 10 of the present invention. In manufacturing the wound dressing delivery system 10 of the present invention, one step is to develop a temporary and releasable bond between film 22 and protective cover 16. In the preferred method of manufacturing system 10, the releasable bond is created by solvent casting film 22 onto protective cover 16. Film 22 is solvent cast onto second surface 20 of protective cover 16. The casting process creates a cohesion force between film 22 and protective cover 16 as previously discussed. The materials and structure of film 22 and protective cover 16 have previously been discussed.

Film 22 may then be coated with an adhesive to form adhesive layer 30. The nature of adhesive layer 30 has previously been discussed. After placing adhesive layer 30 on film 22, a first adhesive strip 38 may be placed on adhesive layer 30 proximate opening end 14, and tacky wound dressing material 51 may be placed on a portion of adhesive layer 30. A tab 46 may be placed over a portion of first adhesive strip 38 opposite adhesive layer 30 to cover the extreme open end 14 portion of adhesive strip 38.

Release liner 58 and protective cover 16 may be sized relative to film 22 and adhesive layer 30 to provide a protective liner overhang 70 and a protective cover overhang 76 as shown in FIG. 3. Protective liner overhang 70 is further sized to extend beyond the extreme pivot end 12 or termination edge of protective cover 16 so that a tape 64 may then be disposed or placed over overhangs 70 and 76 to connect to them. The materials and relative cohesive force developed by these components have previously been discussed.

Although the present invention and its advantages have been described in detail, it should be understood that various changes, substitutions and alterations can be made therein without departing from the spirit and scope of the invention as defined by the appended claims.

What is claimed is:

1. A tacky wound dressing delivery system having a pivot end and for delivering a tacky wound dressing material to a patient, the system further comprising:
    a protective cover having a first side and a second side;
    a film having a first side and a second side, the first side of the film releasably attached to the second side of the protective cover with a first cohesive force;
    an adhesive layer having a first side and a second side, the first side of the adhesive layer being attached to the second side of the film with a second adhesive force;
    the tacky wound dressing material having a first side and a second side, the first side of the tacky wound dressing material attached to a first portion of the second side of the adhesive layer by a third cohesive force, the tacky wound dressing sized smaller than the protective cover or film so that the edges of the tacky wound dressing are covered by the protective cover or film;
    a release liner having a first side and a second side and a first end and a second end, the first side of the release liner adjacent to and releasably secured to the second side of the tacky wound dressing material by a fourth adhesive force and the release liner releasably attached to a second portion of the second side of the adhesive layer by a fifth cohesive force;
    the tacky wound dressing material for releasably attaching to the patient with a sixth cohesive force when exposed and placed against the patient;
    the second portion of the adhesive layer for releasably attaching to the patient with a seventh cohesive force when exposed and placed against the patient;
    the fourth and fifth cohesive forces are weaker than the first, second, and third cohesive forces, the sixth and seventh cohesive forces are stronger than the first, second, and third cohesive forces, and the first cohesive force is weaker than the second, third, sixth and seventh cohesive forces; and
    a pivot assembly connecting the protective cover and the first end of the release liner at an edge proximate the pivot end.

2. The system of claim 1 wherein the tacky wound dressing material comprises a hydrocolloid material.

3. The system of claim 1 wherein the tacky wound dressing material comprises a hydrogel material.

4. The system of claim 1, wherein the film comprises a polyurethane film.

5. The system of claim 1 wherein protective cover comprises a material having a silicone coating on the second side of the protective cover.

6. The system of claim 1, wherein the film comprises a polyurethane film and the protective cover comprises a polyester material with a silicone coating.

7. The system of claim 1, wherein the adhesive layer comprises a pressure-sensitive adhesive.

8. The system of claim 7, wherein the pressure-sensitive adhesive comprises a modified-acrylic based adhesive.

9. The system of claim 1, wherein the release liner comprises a paper with a silicone coating on the first side of the release liner.

10. A tacky wound dressing delivery system for delivering a tacky wound dressing material to a patient's wound, the wound dressing delivery system having a pivot end and an opening end and comprising:
    a film having a first and second side;
    a protective cover having a first side and a second side, the first side of the film temporarily attached to the second side of the protective cover by a releasable bond, the protective cover substantially co-extensive with the film;
    an adhesive layer having a first side and a second side with the first side of the adhesive layer attached to the second side of the film, the adhesive layer substantially co-extensive with the film;
    the tacky wound dressing material having a first side and a second side, the first side of the tacky wound dressing material disposed adjacent to the second side of the adhesive layer and sized smaller than the adhesive layer so that a first portion of the adhesive layer extends beyond the tacky wound dressing material;
    a tab having a first and second side, the first side of the tab attached to a second portion of the second side of the adhesive layer proximate the opening end;
    a release liner having a first and second side, the first side of the release liner releasably attached to the second side of the adhesive layer, a first portion of the release liner extending over the tab, a second portion of the release liner extending beyond the adhesive layer on the pivot end to form a release liner overhang;
    a tape overlying the release liner overhang and a portion of the protective cover proximate the pivot end, thereby connecting the release liner and protective cover; and
    the releasable bond between the protective cover and the film having a first cohesive force, the adhesive layer creating a second cohesive force when placed in contact with the patient's wound and the tacky wound dressing creating a third adhesive force when placed in contact with the patient's wound thereby securing the adhesive layer to the patient, the first cohesive force smaller than the second cohesive force and the third cohesive force.

11. The system of claim 10, wherein the film comprises a polyurethane film.

12. The system of claim 10, wherein protective cover comprises a material having a silicone coating.

13. The system of claim 10, wherein cohesive interaction of the film and protective covering is created by solvent casting of the film onto the protective cover.

14. The system of claim 10, wherein the film comprises a polyurethane film and the protective cover comprises a polyester material with a silicone coating.

15. The system of claim 10, wherein the adhesive layer comprises a pressure-sensitive adhesive.

16. The system of claim 15, wherein the pressure-sensitive adhesive comprises a modified-acrylic based adhesive.

17. The system of claim 10, wherein the release liner comprises a paper with a silicone coating on the first side of the release liner.

18. The system of claim 10, wherein the tape comprises a silicone tape.

19. The system of claim 10 wherein the tacky wound dressing material is a hydrocolloid.

20. The system of claim 10 wherein the tacky wound dressing material is a hydrogel.

21. The system of claim 10 wherein the first side of the tab comprises: a first portion having a substantially non-releasable surface and a second portion have a releasable surface.

22. A dressing delivery system having a pivot end and an opening end for covering a patient's wound, the system comprising:

a polyurethane film having a first side, a second side, a pivot end and an opening end;

a polyester protective cover having a first side and a second side and a pivot end and an opening end, the first side of the film temporarily attached to the second side of the protective cover without requiring an adhesive, the film and protective cover temporarily attached by a temporary bond having a first cohesive force developed by casting the film onto the protective cover;

a protective cover overhang formed on the pivot end of the protective cover by sizing the protective cover so that the protective cover extends beyond the pivot end of the film;

a pressure-sensitive adhesive layer having a first and a second side and disposed on and attached to the second side of the film, the adhesive layer creating a second cohesion force when applied the patient's wound;

a tacky wound dressing material having a first and a second side, the first side of the tacky wound dressing material attached to the second side of the adhesive layer, the tacky wound dressing sized smaller than the adhesive layer;

a tab having a first side and a second side and having a width and a length, the first side of the tab attached to a portion of the second side of the adhesive layer;

a release liner having a first side and second side and a pivot end and an opening end, the first side of the release liner having a silicone coating, and the release liner further having a release liner overhang at the pivot end of the release liner, the first side of the release liner releasably attached to the adhesive layer and the tacky wound dressing material;

a silicone tape overlying a portion of the release liner overhang and the protective cover overhang, the silicone tape securing the protective cover overhang and release liner overhang together; and the first cohesive force being less than the second cohesive force so that after the tab is pulled in a manner to remove the release liner from the adhesive layer and tacky wound dressing material, and the adhesive layer and tacky wound dressing material are applied to the patient's wound, the continued pulling of the release liner will cause the protective cover to release from the film before a force greater than the second cohesion force is reached thereby allowing the removal of all the system except for the film, the tacky wound dressing material, and the adhesive layer.

* * * * *

UNITED STATES PATENT AND TRADEMARK OFFICE
CERTIFICATE OF CORRECTION

PATENT NO. : 5,415,627
DATED : May 16, 1995
INVENTOR(S) : Mark J. Rasmussen, Tod H. Schultz, and Michael B. Killeen, Jr.

It is certified that error appears in the above-indentified patent and that said Letters Patent is hereby corrected as shown below:

Col. 1, ln. 1, insert --
RELATED APPLICATION

This application is related to co-pending patent application Serial No. 08/173,638, filed December 23, 1993, of same assignee (Attorney's Docket 20064-0110).--.

Col. 1, ln. 2, insert --
Technical Field of the Invention

The invention relates to wound dressings, and more particularly to an improved wound dressing delivery system for tacky wound dressings.--

Col. 1, ln. 17, italize *See*.

Col. 6, ln 31, italize *See*.

Signed and Sealed this

Twenty-fourth Day of October, 1995

Attest:

BRUCE LEHMAN

Attesting Officer

Commissioner of Patents and Trademarks